(12) United States Patent
Fukuda et al.

(10) Patent No.: US 7,473,425 B2
(45) Date of Patent: Jan. 6, 2009

(54) REMEDIES FOR ISCHEMIC DISEASE

(75) Inventors: Keiichi Fukuda, 3-2, Sakae-cho, Nerima-ku, Tokyo (JP) 176-0006; Yasuyo Hisaka, 7-16-404, Ogikubo 4-chome, Suginami-ku, Tokyo (JP) 167-0051; Tatsuya Miyai, Tokyo (JP); Masahiko Tamura, Tokyo (JP)

(73) Assignees: Keiichi Fukuda, Tokyo (JP); Yasuyo Hisaka, Tokyo (JP); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/316,890

(22) Filed: Dec. 27, 2005

(65) Prior Publication Data

US 2006/0104942 A1    May 18, 2006

Related U.S. Application Data

(60) Division of application No. 10/392,381, filed on Mar. 20, 2003, which is a continuation-in-part of application No. 10/380,200, filed as application No. PCT/JP01/07946 on Sep. 13, 2001.

(30) Foreign Application Priority Data

Sep. 13, 2000  (JP)  ............................ 2000/277562

(51) Int. Cl.
*A61K 39/00* (2006.01)
*A61K 39/38* (2006.01)

(52) U.S. Cl. .................................. 424/184.1; 424/185.1
(58) Field of Classification Search ....................... None
See application file for complete search history.

(56) References Cited

U.S. PATENT DOCUMENTS

| 6,359,158 B1 * | 3/2002 | Falck et al. ................ 554/219 |
| 6,887,477 B1 * | 5/2005 | Nagano et al. ........... 424/198.1 |
| 2004/0009940 A1 | 1/2004 | Coleman et al. |
| 2004/0019184 A1 * | 1/2004 | Fukuda et al. .............. 530/350 |
| 2004/0131585 A1 * | 7/2004 | Itescu ........................ 424/85.1 |
| 2005/0048026 A1 * | 3/2005 | Miyai et al. ................ 424/85.1 |

FOREIGN PATENT DOCUMENTS

| DE | 100 33 219 A1 | 1/2002 |
| EP | 0 357 240 | 3/1990 |
| WO | WO 99/17798 A1 | 4/1999 |
| WO | WO 99/45775 A1 | 9/1999 |
| WO | WO 9945775 | * 9/1999 |
| WO | WO 01/94420 A1 | 12/2001 |

OTHER PUBLICATIONS

Sullivan et al., Veterinary Surgery, 1993,22, pp. 343-350.*
Henry et al., BMJ 1999, vol. 318, pp. 1536-1539.*
Feldman et al; "Anti-TNFα Therapy Is Useful in Rheumatoid Arthritis and Crohn's Disease: Analysis of the Mechanism of Action Predicts Utility in Other Diseases"; *Transplantation Proceedings*, 30, pp. 4126-4127 (1998).
U. Frank et al; "Treatment of *Staphylococcus aureus* Catheter-Related Infection and Infective Endocarditis with Granulocyte Colony-Stimulating Factor in the Experiment Rabbit Model"; *Antimicrobial Agents and Chemotherapy*, vol. 40, pp. 1308-1310, 1996.
K. Gupta et al; "Angiogenesis: a curse or cure?" www.postgradmedj. com; 81: 236-242, 2005.
P. Huang et al; "Autologous Transplantation of Granulocyte Colony-Stimulating Factor-Mobilized Peripheral Blood Mononuclear Cells Improves Critical Limb Ischemia in Diabetes"; *Diabetes Care*, vol. 28, No. 9, pp. 2155-2160; 2005.
A. Ishida et al; "Autologous Peripheral Blood Mononuclear Cell Implantation for Patients with Peripheral Arterial Disease Improves Limb Ischemia"; *Circ. J.* 69: pp. 1260-1265, 2005.
J. E. Markkanen et al; "Growth factor-induced therapeutic angiogenesis and arteriogenesis in the heart—gene therapy"; *Cardiovascular Research*; vol. 65; pp. 656-664, 2005.
Mestas et al; Of Mice and Not Men: Differences between mouse and Human Immunology; *The Journal of Immunology*, 2004, 172, pp. 2731-238.
K. E. Sullivan et al; "Effects of Perioperative Granulocyte Colony-stimulating factor on Horses with Ascending Colonic Ischemia"; *Veterinary Surgery*; vol. 22, No. 5, pp. 343-350. 1993.
F. Squadrito et al; "The effects of recombinant human granulocyte-colony stimulating factor on vascular dysfunction and splanchnic stimulating factor on vascular dysfunction and splanchnic ischaemia-reperfusion injury"; *British Journal of Pharmacology*, vol. 120, No. 2, pp. 333-339, 1997.

(Continued)

Primary Examiner—Michail A Belyavskyi
(74) Attorney, Agent, or Firm—Browdy and Neimark, P.L.L.C.

(57) ABSTRACT

An effective remedy for ischemic disease, which contains human granulocyte colony-stimulating factor (human G-CSF) and hepatocyte growth factor (HGF) as active ingredients, is disclosed. By administering this remedy, an effective therapy particularly for obstructive arteriosclerosis is provided which can eliminate drawbacks with conventional therapies such as kinesitherapy, pharmacotherapy, revascularization and recently proposed therapies such as gene therapy and intramuscular inoculation of bone marrow cells. Furthermore, the remedy of the present invention can become a remedy for ischemic disease such as ischemic cerebrovascular disorder or ischemic heart disease.

5 Claims, 4 Drawing Sheets

OTHER PUBLICATIONS

Teuveson et al; "New Immunosuppressants: Testing and Development in Animal Models and the Clinic: with Special Reference to DSG"; *Immunological Review*, 1993, N136, pp. 101-107.

Van Noort et al; "Cell Biology of Autoimmune Diseases", *International Review of Sytology*, 1998, v. 178, pp. 127-204.

Orlic et al, "Mobilized bone marrow cells repair the infarcted heart, improving function and survival", Proc. Natl. Acad. Sci. col. 98, No. 18, pp. 10344-10349. Aug. 2001.

Theocharis et al, "Effect of Granulocyte Colony-Stimulating-Factor Administration on Tissue Regeneration Due to Thioacetamide-Induced Liver Injury in Rats", Digestive Diseases and Sciences, vol. 44, No. 10, pp. 1990-1996. Oct. 1999.

Theocharis et al, "Effect of two forms of granulocyte-colony-stimulating factor on hepatic regeneration after 70% partial hepatectomy in rats", Clinical Science, vol. 92, pp. 315-320. 1997.

Orlic, et al, "Bone marrow cells regenerate infarcted myocardium", Nature, vol. 410, pp. 701-705. Apr. 2001.

Penn et al, "Autologous cell transplantation for the treatment of damaged myocardium", Progress in Cardiovascular Diseases, vol. 45, No. 1, pp. 21-32. Jul./Aug. 2002.

Jackson, et al, "Regeneration of ischemic cardiac muscle and vascular endothelium by adult stem cells", Journal of Clinical Investigation. vol. 107, No. 11. Jun. 2001.

Stamm, et al, "Autologous bone-marrow stem-cell transplantation for myocardial regeneration", The Lancet, vol. 361, pp. 45-46. Jan. 2003.

Rafii, et al, "Contribution of marrow-derived progenitors to vascular and cardiac regeneration", Cell & Development Biology, vol. 13, pp. 61-67. 2002.

Makino, et al, "Cardiomyocytes can be generated from marrow stromal cells in vitro", Journal of Clinical Investigation, vol. 103, No. 5, pp. 697-705. Mar. 1999.

Kamihata, et al, "Implantation of bone marrow mononuclear cells into ischemic myocardium enhances collateral perfusion and regional function via side supply of angioblasts, angiogenic ligands, and cytokines", Circulation, vol. 104, pp. 1046-1052. 2001.

Tomita, Shinji, et al, "Autologous Transplantation of Bone Marrow Cels Improves Damaged Heart Function" Circulation, V. 100, Suppl. 19, pp. II-247 to II-256, 1999.

Kobayashi, Masanobu, et al, "Mobilization mechanisms of hematopoietic stem cells into peripheral blood", Igaku No Ayumi, v. 176, No. 9, pp. 558-560, 1996.

Hayashi, Shin-ichiro et al.; *Potential Role of Hepatocyte Growth Factor, a Novel Angiogenic Growth Factor, in Peripheral Arterial Disease, Downregulation of HGF in response to Hypoxia in Vascular Cells*; 1999, pp. II-30-II-308.

* cited by examiner

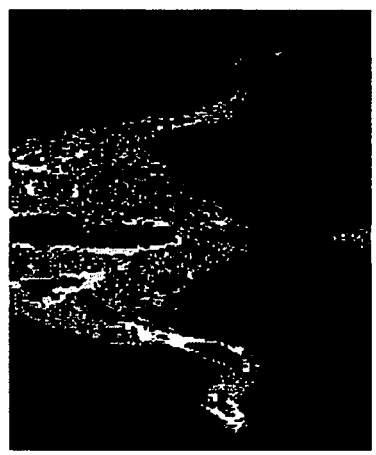
Fig. 4

REMEDIES FOR ISCHEMIC DISEASE

This application is a division of application Ser. No. 10/392,381, filed Mar. 20, 2003, itself a continuation-in-part of U.S. application Ser. No. 10/380,200, filed Mar. 13, 2003 which itself was filed under 35 U.S.C. §371 by entry into the U.S. national stage of a PCT application, PCT/JP01/07946, filed on Sep. 13, 2001.

TECHNICAL FIELD

This invention relates to a remedy for ischemic disease which contains human granulocyte colony-stimulating factor (G-CSF) and hepatocyte growth factor (HGF) as active ingredients.

BACKGROUND ART

The present invention is an invention concerned with remedies for ischemic disease. One typical ischemic disease, obstructive arteriosclerosis, will be described first.

Obstructive arteriosclerosis is a disease in which an arteriosclerotic (atherosclerotic) lesion results in deposition of an atheromatous substance mainly consisting of fats on the endarterium, to arouse occlusion or stenosis of a major truncal artery in the extremity, especially in the lower limb, thereby causing an ischemic disorder in its periphery. Clinical symptoms of this disease are classified as coldness or numbness, intermittent claudication, rest pain, and ulcer/necrosis. In Japan, patients with obstructive arteriosclerosis are estimated to number about 100,000 (Yusuke Tada: Biomedicine & Therapeutics, Vol. 31, 289-292; 1997). The number of patients with this disease is expected to increase because of the increase in the elderly population and the westernization of diets.

Therapies of obstructive arteriosclerosis include kinesitherapy or exercise therapy, pharmacotherapy, and revascularization, which are selected depending on symptoms or the patient's condition. Other measures, now under consideration, for avoiding a resection of a severely ischemic limb are angiogenic therapies (gene therapy, bone marrow autotransplantation, etc.) for promoting angiogenesis. These therapies are currently achieving some success in the treatment of obstructive arteriosclerosis, but the respective therapies involve the following problems.

In some mild cases, the distance of walking has increased in exercise therapy. However, the effect of this therapy is difficult to predict. Moreover, patients are not satisfied with the increase in the walking distance, if any, and 30% of them are reported to have requested revascularization (Takashi Ohta: Japan Medical Journal, Vol. 3935, 25-29, 1999). Thus, at present, this therapy is not a very effective form of treatment.

In pharmacotherapy, antiplatelet agents are mainly prescribed, but they merely prevent an aggravation of symptoms. Microcirculation improving agents and oxygen transport improving agents, which have recently been developed aggressively, are only expected to be indicated for mild cases. Nowadays, there are no radical remedies available for obstructive arteriosclerosis.

Revascularization, on the other hand, is currently the most effective therapy, which involves percutaneous angioplasty or a bypass operation depending on the condition of the patient or the location or extent of the lesion. However, these surgical operations are so extensive that they pose problems, such as surgery-associated complications or death, and a poor prognosis for a long life.

Gene therapy using angiogenic factor is aimed at correcting ischemia by developing collateral circulation channels. Examples of known angiogenic factors are vascular endothelial growth factor (VEGF), epidermal growth factor (EGF), hepatocyte growth factor (HGF), and fibroblast growth factor (FGF). In Japan, clinical studies using human HGF are under way. A method, which involves its intramuscular injection into the lower limb muscle using a plasmid carrying HGF gene, has been investigated in patients with severely ischemic limbs, and expectations are growing for its efficacy. However, this therapy is still at the experimental stage, and evaluations of its safety and efficacy have not been fully carried out. Thus, gene therapy has not become popular.

Intramuscular transplantation of autologous bone marrow cells, which has recently attracted attention, is a therapy in which bone marrow cells are transplanted into the muscle near the diseased part, whereafter they are differentiated into vascular endothelial cells to form blood vessels, thereby treating the diseased part. Bone marrow autotransplantation has no adverse effects on the immune system, and has been recognized to present differentiation of bone marrow cells into endothelial cells or increase the number of blood vessels in animal models. Although its efficacy will have to be evaluated in an increased number of patients, this therapy is expected to become a promising one, because it can treat severe cases. However, the bone marrow is taken under general anesthesia in a clinical setting, so the heavy burden imposed on the patient and medical staff in taking the bone marrow may present problems.

Recent studies have shown that hematopoietic stem cells, which can differentiate into vascular endothelial cells, are present not only in the bone marrow, but also in the peripheral blood, and they take part in angiogenesis (Qun Shi et al., Blood vol. 92, 362-367, 1998; Takayuki Asahara et al., Circulation Research vol. 85, 221-228, 1999; Mario Peichev et al., Blood vol. 95, 952-958, 2000). (The hematopoietic stem cells are called "precursor cells for endothelial cells" from the viewpoint of the function of differentiating into endothelial cells. However, these cells are originally derived from hematopoietic stem cells. Thus, the term "hematopoietic stem cells" is used herein in accordance with the concept that they are a cell population capable of becoming endothelial cells.) Hence, hematopoietic stem cells in the peripheral blood are taken and transplanted into the muscle close to the diseased part, whereby treatment of obstructive arteriosclerosis can be expected. This procedure is advantageous in that the burden imposed on the patient and medical staff at the time of taking peripheral blood stem cells is less than that during transplantation of stem cells present in the bone marrow. Normally, however, the frequency of existence of hematopoietic stem cells in the peripheral blood is extremely low. Thus, it is highly questionable whether a necessary and adequate amount of hematopoietic stem cells for the treatment of obstructive arteriosclerosis can be obtained.

Human G-CSF is a hematopoietic factor discovered as a differentiation/growth factor for progenitor cells of the granulocytic lineage. It is clinically applied as a remedy for neutropenia following bone marrow transplantation or cancer chemotherapy, because it facilitates neutrophilic hematopoiesis in vivo. In addition to this action, human G-CSF acts on hematopoietic stem cells to stimulate their proliferation and differentiation, and also acts to mobilize hematopoietic stem cells present in the bone marrow into the peripheral blood. Actually, based on the latter action, transplantation of the peripheral blood hematopoietic stem cells mobilized by human G-CSF, i.e. peripheral blood stem cell transplantation, is performed in the clinical setting, with the aim of accelerating hematopoietic recovery in cancer patients after intensive chemotherapy. This hematopoietic stem cell mobilizing action of G-CSF is far more potent than that of GM-CSF, also a hematopoietic factor for the granulocytic lineage. In terms of few side effects as well, G-CSF has superiority over GM-CSF.

HGF is a protein which is produced by various mesenchymal cells and targets many epithelial cells, neurons, endothelial cells, and some mesenchymal cells. HGF is known to have cell motility promoting activity and epithelial morphogenesis (luminal structure, etc.) inducing activity, in addition to cell proliferation promoting activity. Since HGF functions as an organ regenerating factor for promoting the regeneration of the kidney, the lung and the digestive tract, as well as the liver, in adults, it is expected to be a remedy for organ disease.

DISCLOSURE OF THE INVENTION

In patients with obstructive arteriosclerosis, administration of human G-CSF prior to treatment with intramuscular transplantation of bone marrow cells can be expected to increase the frequency of hematopoietic stem cells in the bone marrow. Thus, the number of bone marrow punctures for collecting bone marrow cells can be reduced, and the burden on the patient can be reduced. On this occasion, the burden on the patient and the medical staff can be further reduced by obtaining hematopoietic stem cells for transplantation from the peripheral blood. Furthermore, hematopoietic stem cells in the peripheral blood have been shown to contribute to vasculogenesis, so that the increase of hematopoietic stem cells in the peripheral blood induced by the administration of human G-CSF is speculated to promote vasculogenesis. Hence, the mere administration of human G-CSF to patients can be expected to treat obstructive arteriosclerosis. This treatment for obstructive arteriosclerosis by the administration of human G-CSF will clearly reduce the burden on the patient and the medical staff markedly in that it obviates the need for collection and transplantation of hematopoietic stem cells.

Besides, the combined use of human G-CSF and gene therapy using angiogenic factor is expected to enhance the therapeutic effect. That is, G-CSF is caused to act on hematopoietic stem cells, stimulating their proliferation and differentiation. Also, hematopoietic stem cells in the bone marrow are mobilized into the peripheral blood to promote vasculogenesis. At the same time, angiogenesis is promoted by HGF. Effective utilization of these different actions can be predicted to show an additive or synergistic angiogenic effect.

Treatment for obstructive arteriosclerosis using human G-CSF can be expected to take-effect in severe cases, and will be of great benefit to patients. If this treatment is combined with treatment with an angiogenic factor which promotes differentiation and growth of vascular endothelial precursor cells, such as vascular endothelial growth factor (VEGF), epidermal growth factor (EGF), hepatocyte growth factor (HGF) or fibroblast growth factor (FGF), or with the gene therapy of these factors, the therapeutic effect of that treatment is expected to be augmented further. In this case, these factors or their genes can be administered to patients, for example, at sites near the diseased part. Similarly, G-CSF is expected to show an increased therapeutic effect, when combined with agents clinically used as drug therapies for obstructive arteriosclerosis, such as antiplatelet agents, vasodilators, microcirculation improvers, anticoagulants and antilipemic agents.

Furthermore, G-CSF of the present invention is applicable as a remedy for the following diseases, similar ischemic diseases: trauma, rejection reaction during transplantation, ischemic cerebrovascular disorder (such as apoplexy or cerebral infarction), ischemic renal disease, ischemic pulmonary disease, infection-related ischemic disease, ischemic disease of limbs, and ischemic heart disease (such as ischemic cardiomyopathy, myocardial infarction or ischemic heart failure). That is, the present invention provides remedies for these diseases, which contain G-CSF as the active ingredient.

As a result of the foregoing contrivances, we have accomplished the present invention. That is, the present invention provides remedies for ischemic disease, which contain human G-CSF and HGF as active ingredients.

BRIEF DESCRIPTION OF THE DRAWINGS

FIG. 4 is a view showing the effects of administration of physiological saline (control), HGF, G-CSF and HGF+G-CSF, respectively, on the blood flow rate in mice with an ischemic left paw. The red portion represents the highest flow rate, followed by the yellow, green and blue portions in decreasing order.

BEST MODE FOR CARRYING OUT THE INVENTION

Figure 1:
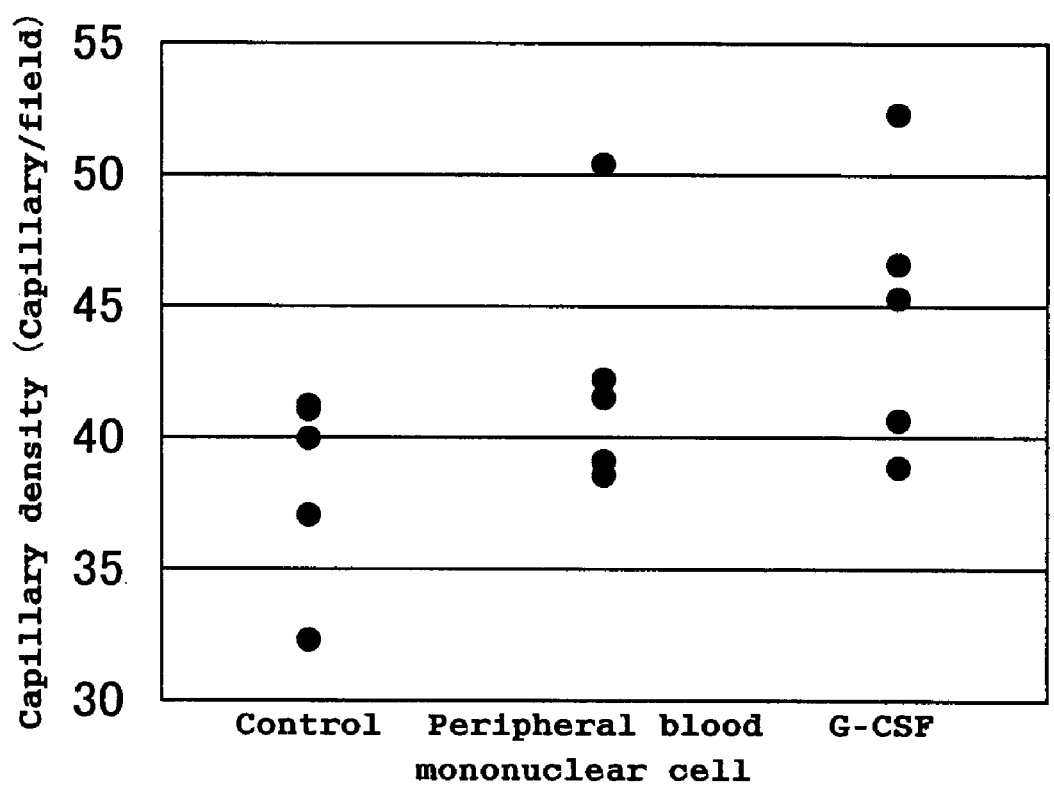
FIG. 1 is a view showing the effects of inoculation of peripheral blood mononuclear cells derived from G-CSF-treated mice and administration of G-CSF, on the density of capillaries in the rat ischemic limb.

Human G-CSF is a known protein composed of 174 amino acid residues.

When G-CSF is used as the active ingredient of the remedy for ischemic disease according to the present invention, any type of G-CSF can be used, but highly purified G-CSF is preferred. Specific examples of G-CSF include mammalian G-CSF, especially human G-CSF, or G-CSF having substantially the same biological activity as mammalian G-CSF. The origin of G-CSF is not limited, and both naturally occurring G-CSF as well as G-CSF obtained by genetic recombination can be used. The G-CSF obtained by genetic recombination may be that having the same amino acid sequence as naturally occurring G-CSF (e.g., JP 1990-5395, JP 1987-236488 A), or that having this amino acid sequence subjected to deletion, substitution and/or addition of one or more amino acids, and having the same biological activity as naturally occurring G-CSF. For example, a polypeptide functionally comparable to G-CSF can be prepared by appropriately introducing a mutation into the amino acid sequence of G-CSF by use of such a method as site-directed mutagenesis (Gotoh, T. et al. (1995) Gene 152, 271-275; Zoller, M. J. and Smith, M. (1983) Methods Enzymol. 100, 468-500; Kramer, W. et al. (1984) Nucleic Acids Res. 12, 9441-9456; Kramer, W. and Fritz H. J. (1987) Methods Enzymol. 154, 350-367; Kunkel, T. A. (1985) Proc. Natl. Acad. Sci. USA, 82, 488-492; Kunkel (1988) Methods Enzymol. 85, 2763-2766). The mutation of an amino acid can occur in the natural world. It is already known that a polypeptide having a certain amino acid sequence modified by deletion and/or addition of one or more amino acid residues and/or substitution of an amino acid for the other amino acid retains the biological activity of the original polypeptide (Mark, D. F. et al., Proc. Natl. Acad. Sci. USA (1984) 81, 5662-5666; Zoller, M. L. & Smith, M. Nucleic Acids Research (1982) 10, 6487-6500; Wang, A. et al., Science (1984) 224, 1431-1433; Dalbadie-McFarland, G. et al., Proc. Natl. Acad. Sci. USA (1982) 79, 6409-6413).

Hence, a polypeptide comprising an amino acid sequence which has one or more amino acid mutations in G-CSF sequence, and being functionally equivalent to G-CSF, can also be used as the remedy for ischemic disease of the present invention. The number of amino acid mutations in such a polypeptide are normally within 30 amino acids, preferably within 15 amino acids, more preferably within 5 amino acids (for example, within 3 amino acids).

In the substitution mutant, substitution of an amino acid for the other amino acid which conserves the nature of the amino acid side chain is desirable. As the amino acid which conserves the nature of the amino acid side chain, there can be named, for example, hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxyl group-containing side chain (S, T, Y), amino acids having a sulfur atom-containing side chain (C, M), amino acids having a carboxylic acid- or an amide-containing side chain (D, N, E, Q), amino acids having a base-containing side chain (R, K, H), and amino acids having an aromatic-containing side chain (H, F, Y, W) (the symbols in the parentheses represent one-letter abbreviations for the corresponding amino acids).

Polypeptides in which a plurality of amino acid residues are added to the amino acid sequence of G-CSF include fusion polypeptides with G-CSF. Such fusion polypeptides are polypeptides produced by fusion between G-CSF and other polypeptide, and can also be used in the present invention. A fusion polypeptide can be prepared by, for example, ligating DNA coding for G-CSF with DNA coding for another polypeptide in-frame, transferring the resulting construct into a suitable expression vector, and expressing the insert in a suitable host. Other polypeptide to be fused to G-CSF is not limited as long as the resulting fusion polypeptide retains biological activity comparable to that of G-CSF.

Numerous reports are already present on G-CSF derivatives with the amino acid sequence of G-CSF changed, and thus these known G-CSF derivatives can be used (for example, U.S. Pat. Nos. 5,581,476, 5,214,132, 5,362,853 and 4,904,584).

Moreover, chemically modified G-CSF can be used. Examples of the chemically modified G-CSF include G-CSF subjected to conformational change, addition or deletion of the sugar chain, and G-CSF to which a compound such as polyethylene glycol has been bound (for example, U.S. Pat. Nos. 5,824,778, 5,824,784, WO 96/11953, WO 95/21629, WO 94/20069, U.S. Pat. No. 5,218,092, JP 1992-164098 A).

G-CSF in the present invention may be produced by any method. For example, it is possible to use G-CSF prepared by culturing a human tumor cell line, followed by extraction, isolation and purification by various methods, or G-CSF prepared by causing *Escherichia coli*; yeast; mammalian cells, such as Chinese hamster ovary cells (CHO cells), C127 cells, COS cells, myeloma cells or BHK cells; or insect cells to perform production by genetic engineering techniques, followed by extraction, isolation and purification by various methods (for example, JP 1989-44200, JP 1990-5395, JP 1987-129298 A, JP 1987-132899 A, JP 1987-236488 A and JP 1989-85098 A).

The method for producing this human G-CSF may be any method which can give the product defined above. Concretely, the human G-CSF is produced using human G-CSF-producing tumor, human G-CSF-producing hybridoma, or a transformed host which has been granted a G-CSF-producing potential by genetic recombination. Depending on the structure of human G-CSF to be produced, a changing operation or various modifying operations are appropriately applied at a suitable stage of the production process. If the human G-CSF is to be produced by genetic recombination, any routinely used host can be employed, such as *Escherichia coli* or animal cells.

HGF is a known heterodimeric protein comprising a 69 kDa α chain and a 34 kDa β chain.

The mode of administration of HGF is not limited, and HGF may be administered as a protein, but it is preferred to administer a gene coding for HGF, as in gene therapy. The gene coding for HGF is generally administered, for example, as an expression vector containing an expression cassette. The vector is not limited, and a non-virus vector may be used, or a virus vector may be used (e.g. Supplementary Volume of Experimental Medicine, "Experimental Methods for Gene Transfer and Expression Analysis," YODOSHA, 1997; Supplementary Volume of Experimental Medicine, "Basic Techniques for Gene Therapy", YODOSHA, 1996). Examples of the vector include a plasmid vector, a virus vector, a phage vector, a cosmid vector and a YAC vector. The expression vector normally includes a regulatory element, such as a promoter, and an antibiotic-resistance gene.

Any methods are available for gene transfer, and include, for example, calcium phosphate transfection, lipofection, a method using a liposome, the naked-DNA method, receptor-mediated gene transfer, a method using a gene gun, DEAE-dextran transfection, and a method using a capillary tube. In the present invention, the gene may be directly transferred into a body, or after gene transfer into cells taken up from the body, the cells may be returned into the body.

Since many reports have been issued on HGF and HGF expression vectors (HGF expression plasmids), those skilled in the art can appropriately select and administer them (e.g. Nakamura, T., Nishizawa, T., Hagiya, M. et al. Nature 1989, 342, 440-443; Hayashi, S., Morishita, R., Higaki, J. et al. Biochem Biophys Res Commun 1996, 220, 539-545; Morishita, R., Sakaki, M., Yamamoto, K. et al. Circulation, 2002, 105, 1491-1496). The administration of the gene encoding HGF can be performed by a method known to those skilled in the art (for example, WO 01/32220, WO 01/26694, WO 97/07824, WO 01/21214).

When HGF is administered as a protein, any type of HGF can be used, but highly purified HGF is preferred. Specific examples of HGF include mammalian HGF, especially human HGF, or HGF having substantially the same biological activity as mammalian HGF. The origin of HGF is not limited, and naturally occurring HGF and HGF obtained by genetic recombination can be used. The HGF obtained by genetic recombination may be that having the same amino acid sequence as naturally occurring HGF (e.g., GenBank Accession Nos.: M73239, M73240, M29145, L02931 and M60718), or that having this amino acid sequence subjected to deletion, substitution and/or addition of one or more amino acids, and having the same biological activity as naturally occurring HGF. For example, a polypeptide functionally comparable to HGF can be prepared by appropriately introducing a mutation into the amino acid sequence of HGF by use of such a method as site-directed mutagenesis (Gotoh, T. et al., 1995, Gene 152, 271-275; Zoller, M. J. and Smith, M., 1983, Methods Enzymol. 100, 468-500; Kramer, W. et al., 1984, Nucleic Acids Res. 12, 9441-9456; Kramer, W. and Fritz, H. J., 1987, Methods Enzymol. 154, 350-367; Kunkel, T. A., 1985, Proc. Natl. Acad. Sci. USA, 82, 488-492; Kunkel (1988) Methods Enzymol. 85, 2763-2766). The mutation of an amino acid can occur in the natural world. It is already known that a polypeptide having a certain amino acid sequence modified by deletion and/or addition of one or more amino acid residues and/or substitution of an amino acid for the other amino acid retains the biological activity of the original polypeptide (Mark, D. F. et al., Proc. Natl. Acad. Sci. USA 81, 1984, 5662-5666; Zoller, M. L. & Smith, M., Nucleic Acids Res. 10, 1982, 6487-6500; Wang, A. et al., Science 224, 1984, 1431-1433; Dalbadie-McFarHand, G. et al., Proc. Natl. Acad. Sci. USA 79, 1982, 6409-6413).

Hence, a polypeptide comprising an amino acid sequence which has one or more amino acid mutation in HGF sequence, and being functionally equivalent to HGF, can also be used as a remedy for ischemic disease of the present invention. The number of amino acid mutations in such a polypeptide is normally within 30 amino acids, preferably within 15 amino acids, more preferably within 5 amino acids (for example, within 3 amino acids).

In the substitution mutants of HGF, substitution of an amino acid for the other amino acid which conserves the nature of the amino acid side chain is desirable, as in the case of G-CSF. Polypeptides in which a plurality of amino acid residues is added to the amino acid sequence of HGF include fusion polypeptides with HGF. Such fusion polypeptides are polypeptides produced by fusion between HGF and other polypeptide, and can also be used in the present invention. A fusion polypeptide can be prepared by, for example, ligating DNA coding for HGF with DNA coding for another polypeptide in-frame, transferring the resulting construct into a suitable expression vector, and expressing the insert in a suitable host. Other polypeptide to be fused to HGF is not limited as long as the fusion polypeptide retains biological activity comparable to that of HGF.

The gene coding for the HGF of the present invention includes a gene coding for such a polypeptide functionally equivalent to the HGF.

Moreover, chemically modified HGF can be used. Examples of the chemically modified HGF include HGF subjected to conformational change, addition or deletion of the sugar chain, and HGF to which a compound such as polyethylene glycol has been bound.

HGF used in the present invention may be produced by any method. For example, it is possible to use HGF prepared by culturing a human tumor cell line, followed by extraction, isolation and purification by various methods, or HGF prepared by causing *Escherichia coli*; yeast; mammalian cells, such as Chinese hamster ovary cells (CHO cells), C127 cells, COS cells, myeloma cells or BHK cells; or insect cells to perform production by genetic engineering techniques, followed by extraction, isolation and purification by various methods. The method for producing this human HGF may be any method which can give the product defined above. Concretely, the human HGF is produced using a transformed host which has been granted an HGF-producing potential by, for example, genetic recombination. Depending on the structure of human HGF to be produced, a changing operation or various modifying operations are appropriately applied at a suitable stage of the production process. If the human HGF is to be produced by genetic recombination, any routinely used host can be employed, such as *Escherichia coli* or animal cells.

The remedy for ischemic disease according to the present invention can contain pharmaceutical carriers and vehicles necessary for assuming the form of a medicinal pharmaceutical composition, and can further contain stabilizers and adsorption preventing agents. Suitable dosage forms can be selected, including injections (such as subcutaneous injection, intradermal injection, intramuscular injection, intravenous injection and intraperitoneal injection), depot preparations, transnasal preparations, oral preparations (such as tablets, capsules, granules, liquids and solutions, and suspensions), transpulmonary preparations, transdermal preparations and transmucosal preparations. If desired, suitable devices can be used.

The remedy for ischemic disease according to the present invention can incorporate, if desired depending on the mode of its administration and its dosage form, a suspending agent, a solution adjuvant, a stabilizer, a tonicity agent, a preservative, an adsorption preventing agent, a surfactant, a diluent, an excipient, a pH regulator, a soothing agent, a buffering agent, a sulfur-containing reducing agent and an antioxidant.

Examples of the suspending agent are methylcellulose, polysorbate 80, hydroxyethylcellulose, acacia, tragacanth powder, sodium carboxymethylcellulose and polyoxyethylene sorbitan monolaurate.

Examples of the solution adjuvant are polyoxyethylene hydrogenated castor oil, polysorbate 80, nicotinamide, polyoxyethylene sorbitan monolaurate, macrogol and castor oil fatty acid ethyl ester.

Examples of the stabilizer are dextran 40, methylcellulose, gelatin, sodium sulfite and sodium metasulfite.

Examples of the tonicity agent are D-mannitol and sorbitol.

Examples of the preservative are methyl p-hydroxybenzoate, ethyl p-hydroxybenzoate, sorbic acid, phenol, cresol and chlorocresol.

Examples of the adsorption preventing agent are human serum albumin, lecithin, dextran, ethylene oxide-propylene oxide copolymer, hydroxypropylcellulose, methylcellulose, polyoxyethylene hydrogenated castor oil and polyethylene glycol.

Examples of the sulfur-containing agent are N-acetylcysteine, N-acetylhomocysteine, thioctic acid, thiodiglycol, thioethanolamine, thioglycerol, thiosorbitol, thioglycollic acid and its salts, sodium thiosulfate, glutathione and those having a sulfhydryl group such as a thioalkanoic acid having 1 to 7 carbon atoms.

Examples of the antioxidant are erythorbic acid, dibutylhydroxytoluene, butylhydroxyanisol, α-tocopherol, tocopheryl acetate, L-ascorbic acid and its salts, L-ascorbyl palmitate, L-ascorbyl stearate, sodium bisulfite, sodium sulfite, triamyl gallate, propyl gallate, and chelating agents such as disodium ethylenediaminetetraacetate (EDTA), sodium pyrophosphate and sodium metaphosphate.

The remedy for ischemic disease of the present invention may further contain normally added ingredients, such as inorganic salts, e.g., sodium chloride, potassium chloride, calcium chloride, sodium phosphate, potassium phosphate and sodium bicarbonate; and organic salts, e.g., sodium citrate, potassium citrate and sodium acetate.

The dose and the frequency of dosing of human G-CSF contained in the remedy for ischemic disease according to the present invention can be determined in consideration of the condition of the patient for whom this remedy is indicated. The dose is usually 0.1 to 500 µg/kg/day, preferably 1 to 50 µg/kg/day, per adult. As the frequency of dosing, the remedy of the invention can be administered once to three times a day, for 1 to 7 days weekly. The mode of administration preferably includes intravenous administration, subcutaneous administration and intramuscular administration.

In the present invention, when HGF gene is administered, choice is made of the mode of administration and the site of administration that are suitable for the disease and symptoms to be treated. The preferred site of administration is the muscle. The preferred mode of administration is the parenteral route.

The dose differs according to symptoms of the patient. When HGF gene is given, its dose per adult is 0.1 µg to 100 mg, preferably 0.001 to 10 mg. When HGF gene is administered in the form of a liposome, its dose per adult is selected from the range of about 1 µg to about 4 mg, preferably the range of about 10 µg to about 400 µg. The frequency of dosing is selected appropriately depending on symptoms of the patient. Preferably, the remedy is administered once in several days to several weeks, more preferably once weekly, totaling a plurality of times, further preferably a total of 8 times.

When HGF is administered as a protein, its dose and frequency of dosing can be determined in consideration of the condition of the patient for whom this remedy is indicated. The dose is usually 0.1 to 500 µg/kg/day, preferably 1 to 50 µg/kg/day, per adult. As the frequency of dosing, the remedy can be administered once to three times a day, for 1 to 7 days weekly. The mode of administration preferably includes intravenous administration, subcutaneous administration and intramuscular administration.

However, the present invention is not limited by the doses of human G-CSF and HGF. In the present invention, G-CSF and HGF can be prepared and administered as a single preparation. Alternatively, they can be prepared separately, and administered on different occasions.

By using the remedy for ischemic disease according to the present invention, the number of hematopoietic stem cells can be increased. The collection of these hematopoietic stem cells from the bone marrow or peripheral blood and their bone marrow autotransplantation to the patient himself or herself can contribute to vasculogenesis in peripheral blood, treating ischemic disease. The administration of the remedy according to the present invention also mobilizes hematopoietic stem cells into the peripheral blood, thus making it possible to treat ischemic disease, without collection or transplantation of hematopoietic stem cells.

Moreover, the remedy of the present invention can be combined with drugs hitherto used with expectation of effectiveness against ischemic disease, such as antiplatelet agents, vasodilators, microcirculation improvers, anticoagulants and antilipemic agents, and can also be used in combination with gene therapy.

The present invention will be described in more detail with reference to Experiments (pharmacological efficacy) and Examples (preparation examples), which in no way limit the present invention.

EXAMPLES

Experiment 1

Pharmacological Efficacy

The left femoral artery and vein of nude mice (BALB/cAJcl-nu) were ligated and then removed to prepare lower limb ischemia models. In an untreated group, the lower limb dropped out in 3 of 5 animals (60%) and became necrotic in 2 animals (40%) two weeks after ischemic treatment. In a group subcutaneously administered G-CSF at a dose of 100 µg/kg/day a total of 5 times from 3 days before creation of lower limb ischemia until 1 postoperative day, the fall of the lower limb occurred in 1 of 5 animals (20%), necrosis in 3 animals (60%) and no damage in 1 animal (20%), 2 weeks after ischemic treatment. Thus, lower limb damage was reduced in the treated group as compared with in the untreated group. These findings show that G-CSF may have the action of alleviating lower limb damage after ischemia by promoting angiogenesis.

Experiment 2

Pharmacological Efficacy

After G-CSF was subcutaneously administered to mice (BALB/cA) at a dose of 100 µg/kg/day for 5 days, the blood was taken, and a mononuclear cell fraction was obtained by the density gradient method (d=1.077). Also, the left femoral artery and vein of nude rats (F344/N Jcl-rnu) were removed to prepare lower limb ischemia models. One day after creation of ischemia, peripheral blood mononuclear cells from the G-CSF-treated mice were intramuscularly inoculated in a dose of about $2 \times 10^7$ cells/head (corresponding to about 5 ml of peripheral blood) to the ischemic limb of the lower limb ischemia nude rat. A control group received an intramuscular administration of phosphate buffer. One week after inoculation, a tissue specimen of the lower limb was prepared, and the density of capillaries was measured after an alkaline phosphatase stain. As a result, the capillary density tended to be higher in the peripheral mononuclear cell treatment group than in the control group (control group: 38.3±1.7, peripheral mononuclear cell treatment group: 42.3±2.1, number of capillaries/field, 5 animals per group, mean±standard error). The results are shown in FIG. 1.

These findings show the possibility that G-CSF promoted the mobilization of endothelial precursor cells to the mouse peripheral blood, thereby promoting angiogenesis in the rats receiving a transplant of the peripheral mononuclear cells, and suggest the possibility of application of G-CSF to the treatment of peripheral circulatory disturbance.

Experiment 3

Pharmacological Efficacy

The left femoral artery and vein of nude rats (F344/N Jcl-rnu) were removed to prepare lower limb ischemia models. The density of capillaries was measured by alkaline phosphatase stain of a lower limb tissue specimen prepared one week after creation of ischemia. Comparisons were made between a group subcutaneously administered G-CSF at a dose of 100 µg/kg/day from 4 days before creation of ischemia until one week after creation of ischemia (G-CSF treatment group) and a control group. The control group received an intramuscular administration of phosphate buffer. As a result, the capillary density was shown to be higher in the G-CSF treatment group than in the control group (control group: 38.3±1.7, G-CSF treatment group: 44.7±2.4, number of capillaries/field, 5 animals per group, mean±standard error). The results are shown in FIG. 1.

These results suggest that G-CSF has the effect of promoting angiogenesis at the site of ischemia, and suggest the possibility of application of G-CSF to the treatment of peripheral circulatory disturbance.

Experiment 4

Pharmacological Efficacy

Figure 2:
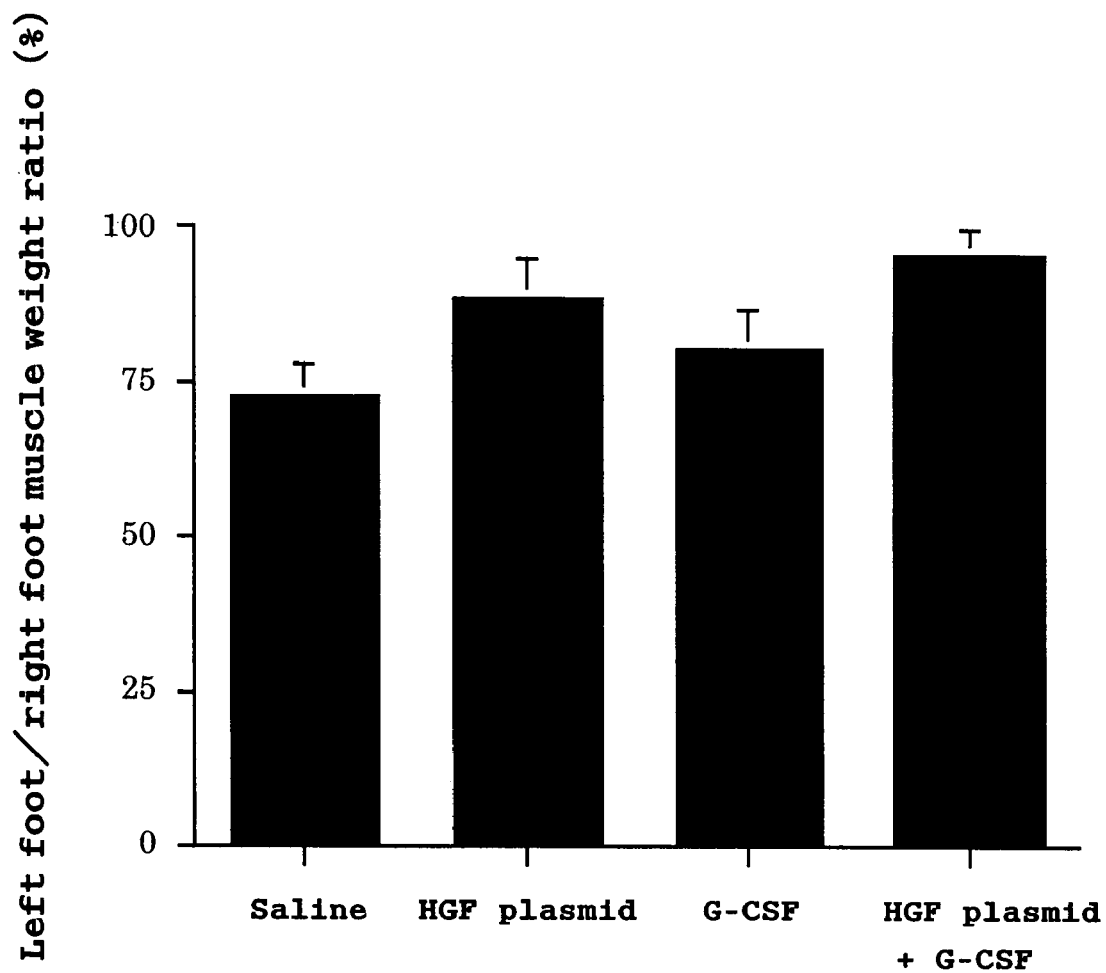
FIG. 2 is a view showing the effects of administration of physiological saline (control), HGF, G-CSF and HGF+G-CSF, respectively, on the lower limb muscle weight ratio (%) in mice with an ischemic left paw.
Figure 3:
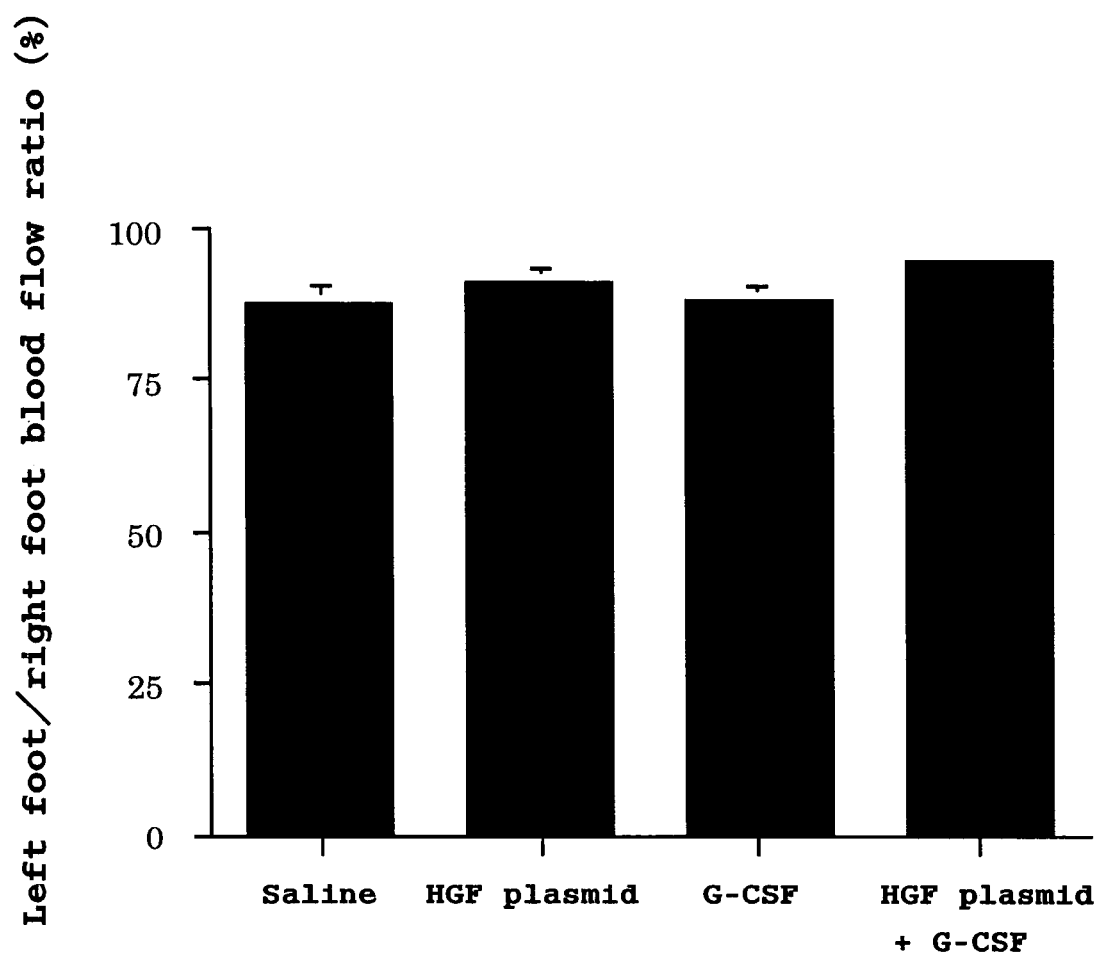
FIG. 3 is a view showing the effects of administration of physiological saline (control), HGF, G-CSF and HGF+G-CSF, respectively, on the lower limb blood flow ratio (%) in mice with an ischemic left paw.

The left femoral artery of wild type mice (C57BL/6), which had received transplantation of bone marrow cells from GFP (green fluorescent protein) transgenic mice after exposure to radiation, was ligated at two locations to prepare lower limb ischemia models. These models were randomly divided into four groups, i.e., a physiological saline treatment group, a G-CSF treatment group, an HGF plasmid treatment group and a G-CSF+HGF plasmid treatment group (5 animals per group). HGF plasmid (Nakamura, T., Nishizawa, T., Hagiya, M. et al., Nature 1989, 342, 440-443; Hayashi, S., Morishita, R., Higaki, J. et al., Biochem Biophys Res Commun 1996, 220, 539-545; Morishita, R., Sakaki, M., Yamamoto, K. et al., Circulation 2002, 105, 1491-1496) was prepared using a plasmid purification kit (manufactured by QIAGEN) in accordance with the manufacturer's protocol. The physiological saline treatment group and the G-CSF (300 µg/kg/day) treatment group received subcutaneous administration for 10 days, beginning 24 hours after surgery. The HGF plasmid treatment group received administration in a dose of 500 µg/kg/day by intramuscular injection performed 24 hours postoperatively. The G-CSF+HGF plasmid treatment group received intramuscular injection of HGF (500 µg/animal) 24 hours postoperatively and, immediately afterwards, received G-CSF treatment (300 µg/kg/day) for 10 days. The drawings show the lower limb muscle weight ratio (FIG. 2), the lower limb blood flow ratio (FIG. 3), and the typical blood flow rate (FIG. 4), 4 weeks after treatment, in each of the groups. The experimental data are shown in Table 1.

cap to obtain a pharmaceutical solution for injection. This preparation for injection is stored in a cold dark place at 10° C. or lower.

Example 2

Preparation Example

Polysorbate 80 (Tween 80: polyoxyethylene sorbitan monooleate), a nonionic surfactant, is added in an amount of 0.1 mg/ml to 100 µg/ml of human G-CSF (10 mM phosphate buffer, pH 7.0), and the mixture is adjusted to an osmotic pressure of 1 using NaCl. Then, the mixed solution is sterilized by filtration through a membrane filter having a pore size of 0.22 µm. The resulting solution is charged into a sterilized vial, whereafter the filled vial is capped with a similarly sterilized rubber stopper and then seamed with an aluminum cap to obtain a pharmaceutical solution for injection. This preparation for injection is stored in a cold dark place at 10° C. or lower.

Example 3

Preparation Example

Polysorbate 20 (Tween 20: polyoxyethylene sorbitan monolaurate), a nonionic surfactant, in an amount of 0.1

TABLE 1

|  | Body weight(g) | | Lower limb muscle weight(g) | | Left foot/right foot muscle weight ratio(%) | Left foot/right foot blood flow ratio(%) |
| --- | --- | --- | --- | --- | --- | --- |
|  | Before experiments | After experiments | Right foot | Left foot | | |
| Physiological saline | 20.28 ± 1.52 | 19.08 ± 1.18 | 0.96 ± 0.05 | 0.70 ± 0.08 | 72.10 ± 5.68 | 87.80 ± 2.92 |
| HGF plasmid | 21.48 ± 0.75 | 19.33 ± 0.23 | 0.88 ± 0.05 | 0.78 ± 0.03 | 88.44 ± 6.11 | 91.43 ± 2.34 |
| G-CSF | 19.04 ± 1.00 | 18.26 ± 0.83 | 0.90 ± 0.03 | 0.72 ± 0.07 | 79.95 ± 6.47 | 88.24 ± 2.55 |
| HGF plasmid + G-CSF | 20.98 ± 0.45 | 19.52 ± 0.55 | 0.92 ± 0.04 | 0.88 ± 0.07 | 95.27 ± 4.29 | 94.56 ± 1.64 |

The G-CSF treatment group and the HGF plasmid treatment group showed a tendency toward improvement over the physiological saline treatment group. In the G-CSF+HGF plasmid treatment group, compared with the other groups, significant improvements were observed in the lower limb muscle weight ratio, the lower limb blood flow ratio and the blood flow rate, showing reduction of damage to the lower limb.

The above results suggested the combination of HGF and G-CSF to enhance a therapeutic effect as compared with HGF or G-CSF administered alone.

Example 1

Preparation Example

Polysorbate 20 (Tween 20: polyoxyethylene sorbitan monolaurate), a nonionic surfactant, is added in an amount of 0.1 mg/ml to 50 µg/ml of human G-CSF (10 mM phosphate buffer, pH 7.0), and the mixture is adjusted to an osmotic pressure of 1 using NaCl. Then, the mixed solution is sterilized by filtration through a membrane filter having a pore size of 0.22 µm. The resulting solution is charged into a sterilized vial, whereafter the filled vial is capped with a similarly sterilized rubber stopper and then seamed with an aluminum mg/ml, 10 mg/ml of HAS and 50 mg/ml of mannitol are added to 50 µg/ml of human G-CSF (10 mM phosphate buffer, pH 7.0), followed by dissolving the mixture. Then, the solution is sterilized by filtration through a membrane filter having a pore size of 0.22 µm. The resulting solution is charged into a sterilized vial, whereafter the filled vial is half capped with a similarly sterilized rubber stopper and lyophilized to obtain a lyophilized preparation for injection. This lyophilized preparation for injection is stored under temperature conditions at room temperature or lower, and is dissolved, just before use, with distilled water for injection.

INDUSTRIAL APPLICABILITY

The remedy for ischemic disease according to the present invention, which contains human G-CSF and HGF as active ingredients, can be expected to show a therapeutic effect in relatively severe cases of obstructive arteriosclerosis, as demonstrated in Experiments 1 to 4. This effect of G-CSF and HGF is inferred to be based on the promotion of angiogenesis. Thus, this remedy can be expected to be therapeutically effective against other ischemic diseases, namely, trauma, rejection reaction during transplantation, ischemic cerebrovascular disorder (such as apoplexy or cerebral infarction), ischemic renal disease, ischemic pulmonary disease, infection-related ischemic disease, ischemic disease of limbs, and ischemic heart disease (such as ischemic cardiomyopathy, myocardial infarction or ischemic heart failure). The therapies according to the present invention are convenient, safe and efficacious as compared with conventional therapies.

What is claimed is:

1. A method for treating ischemic disease of a limb, comprising administering to a subject in need thereof an effective amount of
   (1) a drug clinically used as a pharmacotherapy for ischemic disease,
   in combination with (2) an effective amount of human granulocyte colony-stimulating factor, and
   (3) an effective amount of hepatocyte growth factor wherein the amounts of human granulocyte colony-stimulating factor and hepatocytes growth factor comprises a synergistic combination.

2. The method of claim 1 wherein said drug comprises at least one of any of an antiplatelet agent, a microcirculation improver, an anticoagulant and/or an antilipemic agent.

3. The method of claim 1 wherein said drug, said human granulocyte colony-stimulating factor, and said hepatocyte growth factor are in composition dosage form along with at least one of a suspending agent, a solution adjuvant, a stabilizer, a tonicity agent, a preservative, and absorption prevention agent, a surfactant, a diluents and excipient, a pH regulator, a soothing agent, a buffering agent, a sulfur-containing reducing agent and antioxidant.

4. The method of claim 3 wherein said composition is administered once to three times a day, for 1 to 7 days weekly, by intravenous administration, subcutaneous administration or intramuscular administration.

5. The method of claim 1 wherein said human granulocyte colony-stimulating factor is administered at the rate of 1 to 50 μg/kg/day, and the hepatocyte growth factor is administered at the rate of 0.001 to 10 μg/kg/day.

* * * * *